US00PP25478P3

(12) United States Plant Patent
Kardos

(10) Patent No.: US PP25,478 P3
(45) Date of Patent: Apr. 28, 2015

(54) ***LAGERSTROEMIA* PLANT NAMED 'PIILAG-IV'**

(50) Latin Name: ***Lagerstroemia* L.**
Varietal Denomination: PIILAG-IV

(71) Applicant: Joshua H. Kardos, Watkinsville, GA (US)

(72) Inventor: Joshua H. Kardos, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 189 days.

(21) Appl. No.: 13/815,543

(22) Filed: Mar. 8, 2013

(65) Prior Publication Data

US 2014/0259239 P1 Sep. 11, 2014

(51) Int. Cl.
*A01H 5/00* (2006.01)

(52) U.S. Cl.
USPC ..... Plt./252

(58) Field of Classification Search
USPC ..... Plt./252
See application file for complete search history.

(56) References Cited

U.S. PATENT DOCUMENTS

| | | | |
|---|---|---|---|
| PP10,319 | P | 4/1998 | Whitcomb |
| PP16,917 | P2 | 8/2006 | Dirr |
| PP17,411 | P2 | 2/2007 | Dirr |
| PP21,540 | P2 | 11/2010 | Knight |
| PP22,161 | P2 | 9/2011 | Dirr |
| PP23,071 | P3 | 9/2012 | Dirr |
| PP23,168 | P3 | 11/2012 | Griffith |
| PP23,178 | P3 | 11/2012 | Dirr |
| PP23,518 | P3 | 4/2013 | Kardos |
| 2013/0125275 | P1 | 5/2013 | Kardos |
| 2013/0125276 | P1 | 5/2013 | Kardos |

OTHER PUBLICATIONS

First Editions Collection webpage, (downloaded Mar. 6, 2013, available on Internet in Jan. 2013), "*Lagerstroemia* 'PIILAG-IV'", http://www_._firsteditionsplants_._com /collection, 1 page.
First Editions Collection webpage, (downloaded Mar. 6, 2013, available on Internet in Jan. 2013), "*Lagerstroemia* 'PILLAG-V'", http://www_._firsteditionsplants_._com_/collection, 1 page.
American Nurseryman Catalog, "2013_AN_Woody Plants," Dec. 2012, p. W5.

*Primary Examiner* — Anne Grunberg
(74) *Attorney, Agent, or Firm* — Lathrop & Gage LLP

(57) ABSTRACT

A new and distinct cultivar of *Lagerstroemia* plant named 'PIILAG-IV', characterized by its upright growth habit, dark maroon-purple foliage, red flower buds opening to white flowers, and resistance to powdery mildew and *Cercospora* leaf spot.

3 Drawing Sheets

Genus and species of plant claimed: *Lagerstroemia* L.
Variety denomination: 'PIILAG-IV'.

BACKGROUND OF THE INVENTION

The present invention relates to a new and distinct cultivar of *Lagerstroemia* plant, botanically known as *Lagerstroemia* L., commonly known as crapemyrtle, and hereinafter referred to by the cultivar name 'PIILAG-IV'. 'PIILAG-IV' is grown primarily as an ornamental for landscape use and for use as a potted plant.

'PIILAG-IV' originated in 2010 from open-pollinated seed of *Lagerstroemia* 'Chocolate Mocha' (U.S. Plant Pat. No. 21,540) growing in Watkinsville, Ga. The cultivar 'PIILAG-IV' originated and was selected in a cultivated environment in Watkinsville, Ga. from the progeny of this open-pollination by continued evaluation for growth habit and foliage and flower characteristics.

Asexual reproduction of 'PIILAG-IV' by stem cuttings in Watkinsville, Ga. since 2011 has shown that all the unique features of this new *Lagerstroemia*, as herein described, are stable and reproduced true-to-type through successive generations of such asexual propagation.

SUMMARY OF THE INVENTION

Plants of the new cultivar 'PIILAG-IV' have not been observed under all possible environmental conditions. The phenotype may vary somewhat with changes in light, temperature, soil and rainfall without, however, any variance in genotype.

The following traits have been repeatedly observed and are determined to be unique characteristics of 'PIILAG-IV'. These characteristics in combination distinguish 'PIILAG-IV' as a new and distinct cultivar:

1. Upright growth habit;
2. Dark maroon-purple foliage;
3. Red flower buds opening to white flowers;
4. Resistance to powdery mildew and *Cercospora* leaf spot.

Plants of 'PIILAG-IV' differ from plants of the parent, 'Chocolate Mocha', primarily in foliage and flower color. Plants of 'PIILAG-IV' have dark maroon-purple foliage and white flowers, whereas plants of 'Chocolate Mocha' have dark brown/red-purple foliage and pink flowers.

Plants of 'PIILAG-IV' can be compared to plants of *Lagerstroemia* 'White Chocolate' (unpatented) but differ in growth habit and foliage color. Plants of 'PIILAG-IV' have an upright growth habit and dark maroon-purple foliage, whereas plants of 'White Chocolate' have a rounded growth habit and reddish purple new growth that matures to purplish green.

BRIEF DESCRIPTION OF THE DRAWINGS

The accompanying color photographs illustrate the flower and foliage characteristics and the overall appearance of 'PIILAG-IV', showing the colors as true as it is reasonably possible to obtain in color reproductions of this type. Colors in the photographs may differ slightly from the color values cited in the detailed botanical description which accurately describe the colors of the new *Lagerstroemia*.

DETAILED DESCRIPTION

Figure 1:
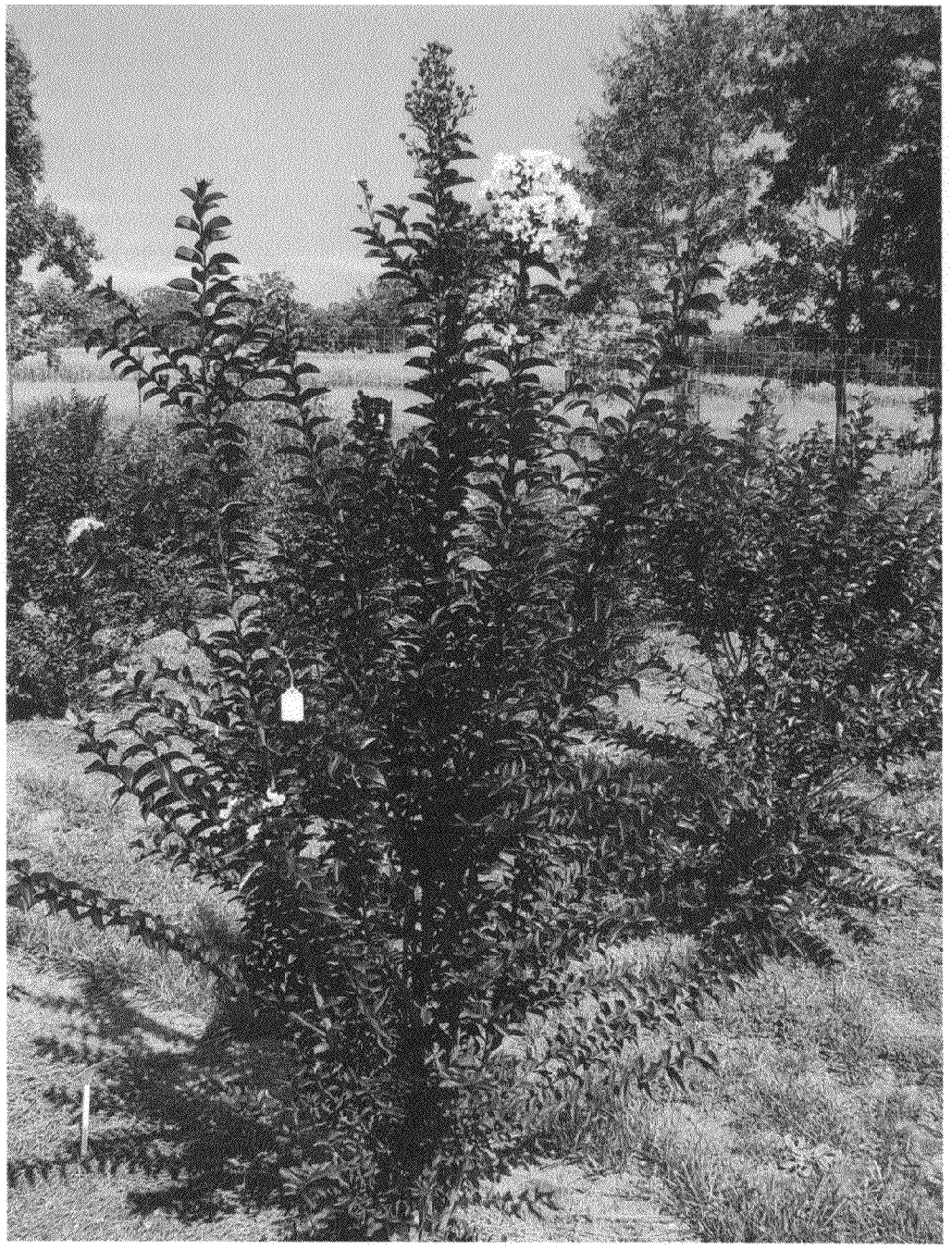
FIG. 1 illustrates the overall appearance of a plant of 'PIILAG-IV' planted in the ground.
Figure 2:
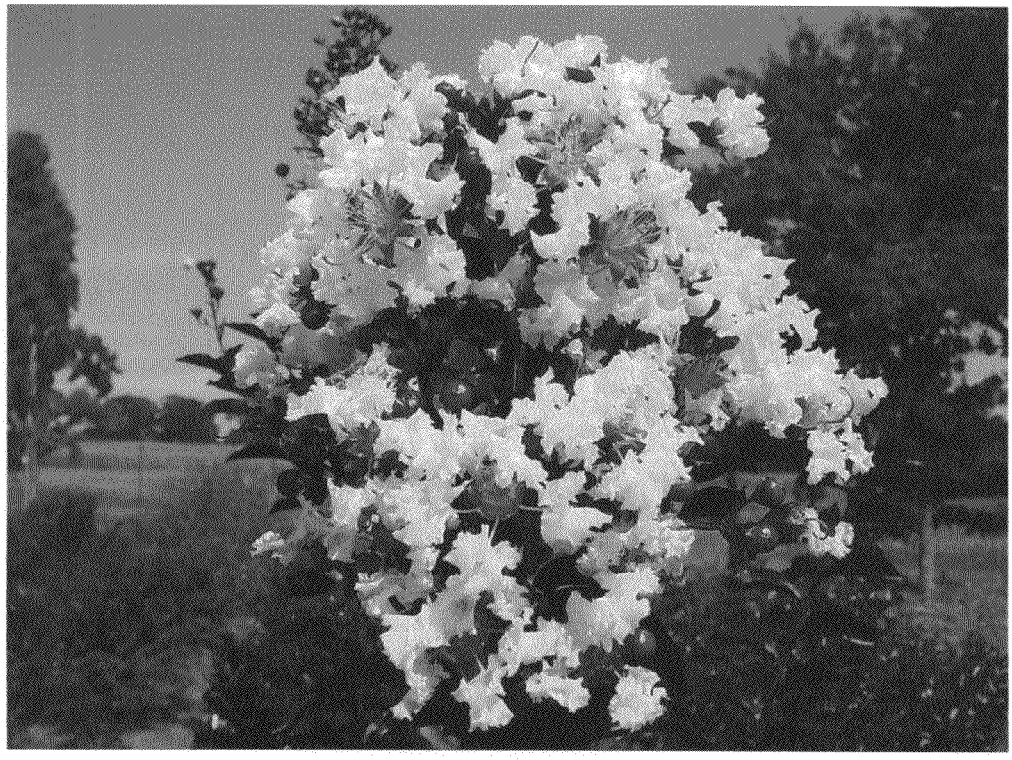
FIG. 2 illustrates a close-up view of the flowers of 'PIILAG-IV'.
Figure 3:
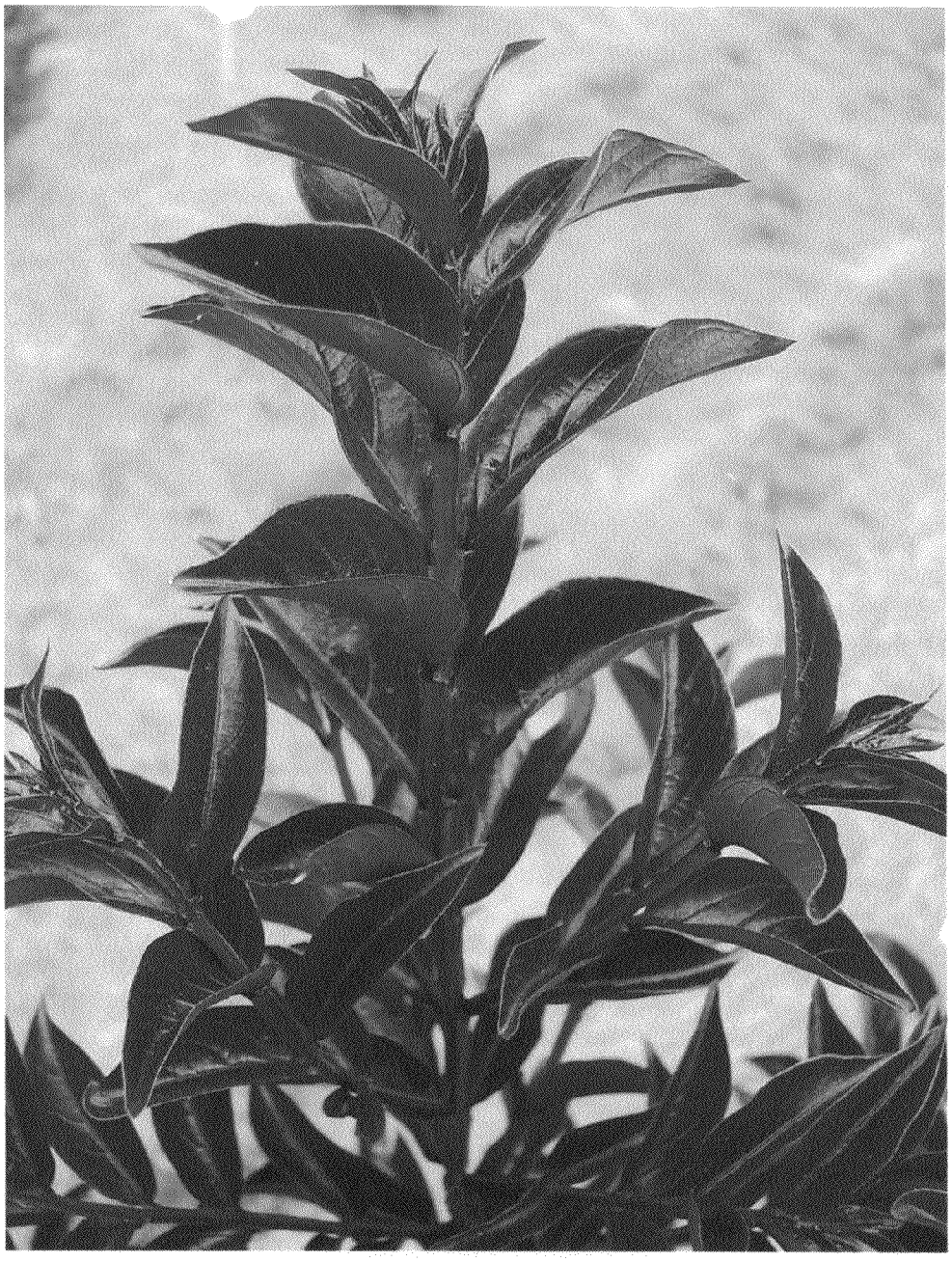
FIG. 3 illustrates a close-up view of the foliage of 'PIILAG-IV'.

In the following description, color references are made to The Royal Horticultural Society Colour Chart, 2007 Edition, except where general terms of ordinary dictionary significance are used. Plants used for the description were approximately two years old and were grown in 11.8 L containers under outdoor conditions in Watkinsville, Ga. Colors are described using The Royal Horticultural Society Colour Chart (R.H.S.).

Botanical classification: *Lagerstroemia* L., cultivar 'PIILAG-IV'.

Parentage:

*Female, or seed, parent.*—*Lagerstroemia* 'Chocolate Mocha' (U.S. Plant Pat. No. 21,540).

*Male, or pollen parent.*—Unknown (open-pollinated).

Propagation: Terminal cuttings.

*Time to initiate roots, summer.*—About 21 days at 32° C.

Plant description: Large flowering shrub or small tree; upright growth habit. Freely branching; pruning enhances lateral branch development.

*Root description.*—Numerous, fine, fibrous and well-branched.

*Plant size.*—The original plant, now about two and a half years old in the ground, is about 203 cm high from the soil level to the top of the inflorescences and about 91 cm wide. First year stems have a diameter of about 2.5 mm. Shape: squarish. Second year and older stems have a diameter of about 5 mm or more. Shape: round.

*Trunk diameter.*—3.6 cm at the soil line.

*Color.*—199A.

*Internode length.*—About 1.6 cm.

*Strength.*—Flexible when young, easily broken once mature.

*First year stem color* (*young*).—183B.

*Color* (*woody*).—200D.

*Second year and older stem color.*—199A.

*Bark.*—Exfoliates in strips beginning on second or third year stems.

Vegetative buds: Sub-opposite to alternate in arrangement, imbricate, conical, with no pubescence.

*Color.*—184A.

*Size.*—About 3 mm in length and 1.3 mm in width.

Foliage description:

*Arrangement.*—Sub-opposite to alternate, simple.

*Length.*—About 4.5 cm.

*Width.*—About 2.8 cm.

*Shape.*—Elliptical.

*Apex.*—Acuminate.

*Base.*—Cuneate.

*Margin.*—Entire.

*Texture* (*upper and lower surfaces*).—Glabrous and glossy.

*Venation pattern.*—Pinnate.

*Venation color of emerging foliage* (*upper surface*).—187A.

*Venation color of emerging foliage* (*lower surface*).—185A.

*Venation color of fully expanded foliage* (*upper surface*).—187A.

*Venation color of fully expanded foliage* (*lower surface*).—184B.

*Color in developing foliage* (*upper surface*).—187A.

*Color in developing foliage* (*lower surface*).—185A.

*Color in fully expanded foliage* (*upper surface*).—187A.

*Color in fully expanded foliage* (*lower surface*).—184B.

*Petiole length.*—About 2 mm.

*Petiole diameter.*—About 1 mm.

*Petiole color* (*upper and lower surfaces*).—N186C.

*Pubescence.*—None.

Flower description: Flowers are produced from about August to September in Watkinsville, Ga. An inflorescence is showy for about two weeks, and individual flowers last about one day and are self-cleaning.

*Inflorescence type.*—Panicle.

*Inflorescence length.*—About 12.4 cm.

*Inflorescence width.*—About 10.9 cm.

*Peduncle.*—About 10.4 cm in length, about 2 mm in diameter, color is 183B, and no pubescence.

*Individual flowers.*—About 2 cm in height and 3.4 cm in diameter.

*Flower buds.*—Length: about 7 mm; Diameter: about 7 mm; Color: 60A.

*Pedicels.*—About 7 mm in length, 183B in color, and no pubescence.

*Calyx.*—About 7 mm in length, about 1 cm in diameter, 60A in color, and no pubescence.

Petals:

*Arrangement/appearance.*—Usually 6 or 7 per flower.

*Petal length.*—About 1.7 cm.

*Petal width.*—About 1.4 cm.

*Petal shape.*—Fan-shaped.

*Petal apex.*—Ruffled, rounded.

*Petal base.*—Sagittate.

*Petal margin.*—Ruffled.

*Petal texture* (*upper and lower surfaces*).—Glabrous.

*Petal color.*—Upper and lower surfaces are NN155D.

Stamens:

*Quantity/arrangement.*—About 25 to 30 short stamens clustered in the center, about 7 mm long, filament color is 2D, and anther color is 14C. The short stamens are surrounded by 6 longer stamens, about 1.2 cm long, filament color is 36B, and anther color is 14C. The stamens are not pubescent.

*Pollen.*—Produced in moderate quantities and is 13B in color on the short and long stamens.

Pistils:

*Quantity.*—One superior pistil per flower.

*Pubescence.*—None.

*Pistil length.*—About 1.7 cm in length.

*Stigma shape.*—Round, about 1 mm in diameter.

*Stigma color.*—148A.

*Style color.*—178C and about 1.4 cm in length.

*Ovary color.*—11C and about 2 mm in diameter.

Fruit:

*Type/appearance.*—Six-valved, dehiscent, broad ellipsoidal capsule.

*Length*.—About 8 mm.

*Diameter*.—About 7 mm.

*Immature color*.—144A.

*Mature color*.—200C. Each capsule contains many seeds that are about 5 mm long, 3 mm wide, and 200C in color.

Disease/pest resistance: Plants of the claimed *Lagerstroemia* variety grown in field and container trials have exhibited resistance to powdery mildew and *Cercospora* leaf spot.

I claim:

1. A new and distinct *Lagerstroemia* plant named 'PIILAG-IV', as illustrated and described herein.

* * * * *